(12) United States Patent
Uchegbu et al.

(10) Patent No.: US 10,213,474 B2
(45) Date of Patent: Feb. 26, 2019

(54) DELIVERY OF DRUGS

(71) Applicant: Nanomerics LTD, St Albans, Hertfordshire (GB)

(72) Inventors: Ijeoma Uchegbu, St Albans (GB); Andreas Schatzlein, St Albans (GB); Lisa Godfrey, Chelmsford (GB); Katerina Lalatsa, Portsmouth (GB); Antonio Iannitelli, Greater London (GB)

(73) Assignee: Nanomerics LTD, St Albans Hertfordshire (GB)

( * ) Notice: Subject to any disclaimer, the term of this patent is extended or adjusted under 35 U.S.C. 154(b) by 0 days.

(21) Appl. No.: 15/034,321

(22) PCT Filed: Nov. 3, 2014

(86) PCT No.: PCT/GB2014/053254
§ 371 (c)(1),
(2) Date: May 4, 2016

(87) PCT Pub. No.: WO2015/063510
PCT Pub. Date: May 7, 2015

(65) Prior Publication Data
US 2016/0279189 A1 Sep. 29, 2016

(30) Foreign Application Priority Data

Nov. 4, 2013 (GB) .................... 1319437.8

(51) Int. Cl.
*A61K 9/00* (2006.01)
*A61K 9/16* (2006.01)
(Continued)

(52) U.S. Cl.
CPC ............ *A61K 38/08* (2013.01); *A61K 9/0043* (2013.01); *A61K 9/0085* (2013.01);
(Continued)

(58) Field of Classification Search
CPC ...... A61K 38/08; A61K 47/36; A61K 9/1652; A61K 9/5161; A61K 9/0043
See application file for complete search history.

(56) References Cited

U.S. PATENT DOCUMENTS 6,107,271 A * 8/2000 Moskal .............. C07K 5/06165
514/17.3
7,662,403 B2 * 2/2010 Dyer .................... A61K 9/0043
424/434
(Continued)

FOREIGN PATENT DOCUMENTS

JP 2010-031218 A 2/2010
JP 2010-506827 A 3/2010
(Continued)

OTHER PUBLICATIONS

Hertzog et al. (Type I interferon receptors, biochemistry and biological functions, J. Bio. Chem., 2007, vol. 282, pp. 20053-20057).*
(Continued)

*Primary Examiner* — Kortney L. Klinkel
(74) *Attorney, Agent, or Firm* — Saliwanchik, Lloyd & Eisenschenk (57) ABSTRACT

The present invention relates to a composition comprising a hydrophilic drug and an amphiphilic carbohydrate compound for use in therapy wherein the composition is intranasally administered to the human or animal body. The composition can be used to treat a variety of disorders, including schizophrenia, obesity, pain and sleep disorders, psychiatric diseases, neurodegenerative conditions, brain cancers and infective diseases.

8 Claims, 2 Drawing Sheets

(51) Int. Cl.
　　　A61K 9/51　　　(2006.01)
　　　A61K 38/08　　　(2006.01)
　　　A61K 47/36　　　(2006.01)
(52) U.S. Cl.
　　　CPC .......... *A61K 9/1652* (2013.01); *A61K 9/5161* (2013.01); *A61K 47/36* (2013.01)

(56) References Cited

U.S. PATENT DOCUMENTS

| | | | | |
|---|---|---|---|---|
| 7,859,926 | B2* | 12/2010 | Takami | G11C 7/067 365/189.02 |
| 8,278,277 | B2* | 10/2012 | Uchegbu | A61K 47/48907 514/18.5 |
| 8,920,819 | B2* | 12/2014 | Uchegbu | A61K 47/48907 424/400 |
| 2010/0222281 | A1 | 9/2010 | Uchegbu et al. | |
| 2012/0258176 | A1* | 10/2012 | Sung | A61K 9/5146 424/491 |
| 2013/0183244 | A1* | 7/2013 | Hanes | A61K 9/0085 424/9.1 |
| 2013/0209545 | A1* | 8/2013 | Twidwell | A61K 31/4422 424/450 |

FOREIGN PATENT DOCUMENTS

| | | |
|---|---|---|
| WO | WO-2004/026912 A1 | 4/2004 |
| WO | WO-2008/017839 A1 | 2/2008 |

OTHER PUBLICATIONS

Heras et al. (Chitosan Amphiphilic derivatives. Chemistry and Application, Current Organic Chem., 2010, pp. 308-330).*

Simmons et al., Surgical Management of airway obstruction during sleep, Laryngoscope, 1977, vol. 87, pp. 326.*

Kumar et al. (Evaluation of neuropeptide loaded trimethyl chitosan nanoparticles for nose to brain delivery, Int. J. Biolog. Macromolecules, 2013, vol. 61, pp. 189-195) (Year: 2013).*

Veronesi et al. in Chapter 20, Intranasal delivery of neuropeptides, Merighi Ed. Neuropeptides, methods and protocols, Springer Protocal, Humana Press, 2011, London, p. 304 (Year: 2011).*

Salio et al. in Chapter 3, Combined light and electronmicroscope visualization of neuropeptides and their receptors in centralneurons, Merighi Ed. Neuropeptides, methods and protocols, Springer Protocal, Humana Press, 2011, London, p. 57-58 (Year: 2011).*

Merck Manual of Medical Information , 2000, p. 277-278 (Year: 2000).*

Burbach in What are neuropeptides, Chapter 1, Merighi Ed. Neuropeptides, methods and protocols, Springer Protocal, Humana Press, 2011, London, p. 6-7 (Year: 2011).*

Merck Manual of Medical Information , 2000, p. 839-840 (Year: 2000).*

Civelli et al. in Orphan receptors, novel neuropeptides and reverse pharmaceutical research, Brain Research, 1999, vol. 848, pp. 63-65 (Year: 1999).*

International Search Report dated May 7, 2015 in International Application No. 2015/063510.

Kumar et al., "Evaluation of Neuropeptide Loaded Trimethyl Chitosan Nanoparticles for Nose to Brain Delivery", International Journal of Biological Macromolecules, Jul. 2, 2013, vol. 61, pp. 189-195, Elsevier.

Uchegbu et al., "Polymeric Chitosan-based Vesicles for Drug Delivery", Journal of Pharmacy and Pharmacology, May 1, 1998, vol. 50, No. 5, pp. 453-458, John Wiley & Sons, Ltd., London.

Artursson, Per et al., Effect of Chitosan on the Permeability of Monolayers of Intestinal Epithelial Cells (Caco-2), Pharmaceutical Research, 1994, 11(9):1358-1361, Plenum Publishing Corporation.

Bernkop-Schnürch et al., Novel Bioadhesive Chitosan-EDTA Conjugate Protects Leucine Enkephalin from Degradation by Aminopeptidase N, Pharmaceutical Research, 1997, 14(7):917-922, Plenum Publishing Corporation.

Abdel Mouez, Mamdouh et al., Bioavailability enhancement of verapamil HCl via intranasal chitosan microspheres, European Journal of Pharmaceutical Sciences, 2014, 51:59-66, Elsevier B.V.

Polnok, A. et al., Influence of methylation process on the degree of quaternization of N-trimethyl chitosan chloride, European Journal of Pharmaceutics and Biopharmaceutics, 2004, 54(1):77-83, Elsevier B.V.

Siew, Adeline et al., Enhanced Oral Absorption of Hydrophobic and Hydrophilic Drugs Using Quaternary Ammonium Palmitoyl Glycol Chitosan Nanoparticles, Molecular Pharmaceutics, 2012, 9(1):14-28, American Chemical Society.

Thanou, M.M. et al., Effect of degree of quaternization of N-trimethyl chitosan chloride for enhanced transport of hydrophilic compounds across intestinal Caco-2 cell monolayers, Journal of Controlled Release, Feb. 2000, 64(1-3):15-25, Elsevier Science B.V.

Zhang, Xingguo et al., Brain pharmacokinetics of neurotoxin-loaded PLA nanoparticles modified with chitosan after intranasal administration in awake rats, Drug Development and Industrial Pharmacy, 2013, 39(11):1618-1624, Informa Healthcare USA, Inc.

Sieval, A. B. et al., Preparation and NMR characterization of highly substituted N-trimethyl chitosan chloride, Carbohydrate Polymers, 1998, 36(2-3):157-165, Elsevier Science Ltd.

Office Action dated Jul. 11, 2018 in Japanese Application No. 2016-256933, along with its English translation.

Uchegbu, I.P. et al., "Polymeric Chitosan-based Vesicles for Drug Delivery", *J. Pharm. Pharmocol.*, 1998, 50:453-458, 1998 J. Pharm. Pharmocol.

Kumar, M. et al., "Evaluation of neuropeptide loaded trimethyl chitosan nanoparticles for nose to brain delivery", *Internation Journal of Biological Macromolecules*, 2013, 61:189-195, 2013 Elsevier B.V.

Teijeiro-Osorio, D. et al., "New Generation of Hybrid Poly/Oligosaccharide Nanoparticles as Carriers for the Nasal Delivery of Macromolecules", *Biomacromolecules*, 2009, 10:243-249, 2009 American Chemical Society.

Office Action dated Nov. 6, 2018 in Japanese Application No. 2016-526933, along with its English translation.

* cited by examiner

DELIVERY OF DRUGS

CROSS-REFERENCE TO RELATED APPLICATIONS

This application is the U.S. national stage application of International Patent Application No. PCT/GB2014/053254, filed Nov. 3, 2014, which claims the benefit of United Kingdom Patent Application No. 1319437.8, filed Nov. 4, 2013.

FIELD OF THE INVENTION

The present invention relates to a new system for the intranasal delivery of drugs to the brain.

BACKGROUND TO THE INVENTION

The treatment of diseases of the brain is significantly limited by the blood brain barrier. Over the last decade intranasal administration of drugs has gained increasing interest as a non-parenteral therapy. Originally seen as a route of administration for the local treatment of congestion, infection, rhinitis or nasal polyposis, in recent years a variety of products have entered the market for the systemic treatment of a variety of ailments. Nasal delivery of drugs has many advantages, including avoidance of first pass metabolism and degradation in the gut, rapid onset with quick diffusion into the systemic system that parallels with intravenous administration and patient compliance due to the non-invasive nature and ease of self-medication.

Within the nasal passage there are two main areas of absorption: the respiratory zone, which has the largest surface area and is highly vascularised, where active principles can cross the epithelium via para-or-transcellular routes, and the olfactory epithelium. The latter comprises only 3-5% of the total surface area of the nasal cavity and therefore is not largely involved in systemic absorption, but can allow direct access to the CNS, bypassing the blood brain barrier via the processes of olfactory neurons, through to the synaptic junctions with neurons of the olfactory bulb.

There are physical disadvantages associated with administration via the nasal route that must be overcome. These include mucociliary clearance, enzymatic activity of the nasal mucosa, peptidases and drug metabolising enzymes. In addition, molecular weight and lipophilicity play a part in absorption—low molecular weight molecules having a molecular weight less than 300 Da tend to be rapidly absorbed whereas for molecules between 300-1000 Da, liposolubility is an important property. Lipophilic molecules diffuse freely, whereas it is thought that hydrophilic molecules must pass through the paracellular route. Molecules with a molecular weight above 1 kDa absorb very slowly and have a low bioavailability. These barriers can be addressed by altering the physiochemical properties of the molecule, increasing permeability by coadministration of an absorption promoter or reducing excretion/degradation by co-administering inhibitors. Absorption promoters currently under development include alkylsaccharides (Intravail®), chitosan (ChiSys™), low methylated pectin (PecSys™) and polyethylene glycol (30%).

Chitosan and its derivatives are commonly used as absorption enhancers due to chisosan's well documented ability to facilitate paracellular transport by opening the tight junctions or by interacting with extra-cellular matrix components. Chitosan increases the bioavailability of verapamil when administered nasally to rabbits in comparison to nasal verapamil solution (Abdel Mouez et al; Eur J Pharm Sci 2013, 30, 59-66). In addition, polylactic acid nanoparticles modified with chitosan have been used to encapsulate the analgesic peptide Neurotoxin. Rats intranasally administered with these chitosan modified nanoparticles had an increased concentration of neurotoxin in the periaqueductal gray in comparison to polylactic acid alone loaded nanoparticles (Zhang et al; Drug Development and Industrial Pharmacy 2013, 39, (11), 1618-24).

Endogenous opioid peptides Leucine5-enkephalin (LENK) and Methionine5-enkephalin (MENK) are mainly degraded by cleavage of the N-terminal tyrosine. In the presence of polycarbophil-cysteine (0.25%) and glutathione (1%) LENK has shown reduced degradation and enhanced transportation across freshly excised bovine nasal mucosa. The absorption enhancer sodium glycocholate and protease inhibiter puromycin co-administered with LENK reduced degradation in nasal washings. However this combination of excipients can lead to cell leakage and therefore toxicity.

Chitosan formulations can also reduce the degradation of peptides. For instance, a chitosan-EDTA conjugate has been shown to reduce the degradation of LENK (Bernkop-Schnürch et al; 1997, Pharm Res 14, 917-22). LENK has also been nasally administered with trimethyl chitosan nanoparticles and shown enhanced antinociception in two mouse pain models in comparison to LENK alone (Kumar et al; Int J Biol Macromol 2013, 61C, 189-195).

WO2004/026912 describes polysaccharides which are used to solubilise hydrophobic drugs. The polysaccharides are amphiphilic and are generally selected from any derivatives of the following: chitosans, dextrans, alginic acids, starches, dextran and guar gums. Quaternary ammonium palmitoyl glycol chitosan (GCPQ) and quaternary ammonium hexadecyl glycol chitosan (GCHQ) are used in the Examples of this patent application as solubilising polysaccharides.

WO2008/017839 describes micellar clusters formed from amphiphilic carbohydrate polymers and their use in formulating hydrophobic drugs. GCPQ is specifically exemplified as an amphiphilic carbohydrate polymer.

In U.S. Pat. No. 8,278,277 a lipid ester prodrug of LENK is formed and added to a composition comprising GCPQ. The compositions are delivered intravenously or orally. The prodrug was converted to LENK in vivo and shown to result in significant LENK brain levels. However, none of these prior art patent publications discuss formulations involving hydrophilic drugs per se.

SUMMARY OF THE INVENTION

In accordance with a first aspect of the invention there is provided a composition comprising a hydrophilic drug and an amphiphilic carbohydrate compound for use in therapy wherein the composition is intranasally administered to the human or animal body.

In accordance with a second aspect of the invention there is provided a pharmaceutical composition suitable for intranasal administration comprising an amphiphilic carbohydrate compound and a hydrophilic drug and one or more pharmaceutically acceptable excipients.

The amphiphilic carbohydrate compound is capable of self-assembly into nanoparticles in aqueous media.

Although chitosan and its derivatives are well documented for the delivery of drugs via the nasal route, nasal delivery with self-assembling amphiphilic carbohydrates such as GCPQ has not been reported. Unlike chitosan, which is soluble at acidic pH, GCPQ is capable of self-assembly at neutral pH, and this confers an advantage over its parent compound for nasal delivery. We believe that the addition of the palmitoyl chain to chitosan enables this chitosan derivative to self-assemble and confers greater association with drug compounds and therefore enhanced delivery.

Furthermore, GCPQ is not thought to function in the same manner as the documented chitosan derivatives. Chitosan (Artusson, P., et al; 1994. 11 1358-1361) and trimethyl chitosan (Thanou, M. M., et al; Journal of Controlled Release, 2000, 64, 15-25) open intercellular tight junctions and are believed to promote membrane permeabilisation and hydrophilic drug absorption through this mechanism even when administered intranasally (Kumar, M., et al; International Journal of Biological Macromolecules, 2013, 61, 189-95). Amphiphilic self-assembling chitosans such as GCPQ amphiphiles do not open intercellular junctions (Siew, A., et al; Molecular Pharmaceutics, 2012, 9, 14-28). Hence the ability of amphiphilic carbohydrate compounds such as GCPQ to facilitate the delivery of hydrophilic drugs was unexpected.

DETAILED DESCRIPTION OF THE INVENTION

By hydrophilic, is meant a compound with high water solubility ($>1$ mg mL$^{-1}$). The invention has particular utility for the delivery of hydrophilic drugs to the brain. We have shown that the drug, delivered in accordance with the invention, is able to have a therapeutic effect in the brain.

The hydrophilic drug is preferably a peptide. Peptides are of tremendous clinical value for the treatment of many central nervous system (CNS) disorders, and preferably therefore the drug is a CNS active drug. Many existing peptide pharmaceuticals are rendered ineffective after oral administration or are unable to cross the blood brain barrier (BBB) mainly due to their hydrophilicity, size, charge and rapid metabolic degradation in the gastrointestinal tract, nasal cavity and blood, as detailed above. Since the invention has particular utility for delivering drugs to the brain, the hydrophilic drug is preferably a neuroactive agent.

Endogenous opioid neuropeptides, preferably neuropentapeptides are particularly preferred drugs for use in this invention. Examples include MENK and LENK.

The drug may be used to treat brain disorders such as schizophrenia, obesity, pain and sleep disorders, psychiatric diseases, neurodegenerative conditions, brain cancers and infective diseases.

Preferred drugs include neuropeptides: enkephalin, neuropeptide S, dalargin, orexin, vasopressin, leptin, cholecystokinin, dynorphin, detorphin I, neurotensin and oxytocin.

The amphiphilic carbohydrate compound is typically selected from chitosans, dextrans, alginic acids, starches, guar gums, and their derivatives. Preferably the amphiphilic compound is a chitosan derivative.

In a preferred embodiment of the invention, the amphiphilic carbohydrate compound is represented by the formula:

wherein $a+b+c+d=1.000$ and
a is between 0.00 and 0.970
b is between 0.01 and 0.990,
c is between 0.000 and 0.970, and
d is between 0.01 and 0.990;
and wherein:
X is a hydrophobic group;
$R_1$, $R_2$ and $R_3$ are independently selected from a substituted or unsubstituted alkyl group;
$R_4$, $R_5$, $R_6$ and $R_{10}$ are independently selected from hydrogen, a substituted or unsubstituted alkyl group, a substituted or unsubstituted ether group, or a substituted or unsubstituted alkene group;
$R_7$ may be present or absent and, when present, is an unsubstituted or substituted alkyl group, an unsubstituted or substituted amine group or a substituted or unsubstituted amide group;
$R_8$ and $R_9$ are independently selected from hydrogen and either a substituted or unsubstituted alkyl group, a substituted or unsubstituted ether group, or a substituted or unsubstituted alkene group;
or a salt thereof.

In the above general formula, the a, b, c and d units may be arranged in any order and may be ordered, partially ordered or random. The * in the formula is used to indicate the continuing polymer chain. In preferred embodiments, the molar proportion of the d units is greater than 0.01, and more preferably is at least 0.110, more preferably is at least 0.120, more preferably is at least 0.150 or in some embodiments is at least 0.18. Generally, the molar proportion of the d unit is 0.500 or less, and more preferably is 0.350 or less.

Preferably, the molar proportion of the b unit is between 0.010 and 0.800, and more preferably between 0.050 and 0.600.

Preferably, the molar proportion of the c unit is between 0.0200 and 0.850, and more preferably between 0.05 and 0.550.

Preferably the molar proportion of the a unit is between 0.05 and 0.85 and more preferably between 0.10 and 0.75.

As can be seen from the above formula, the a and c units may optionally be absent. The d units provide the first portion of the monomer units that are derivatised with a hydrophobic group, and the b units provide the second portion of the monomer units and are derivatised with a quaternary nitrogen group. When present, the a units provide the third group of monomer units in which the amine groups are derivatised in a different manner to the first or second group.

When present the c units provide the fourth group of monomer units in which the amine groups are underivatised.

In the present invention, the hydrophobic group X is preferably selected from a substituted or unsubstituted group which is an alkyl group such as a $C_{4-30}$ alkyl group, an alkenyl group such as a $C_{4-30}$ alkenyl group, an alkynyl group such as a $C_{4-30}$ alkynyl group, an aryl group such as a $C_{5-20}$ aryl group, a multicyclic hydrophobic group with more than one $C_4$-$C_8$ ring structure such as a sterol (e.g. cholesterol), a multicyclic hydrophobic group with more than one $C_4$-$C_8$ heteroatom ring structure, a polyoxa $C_1$-$C_4$ alkylene group such as polyoxa butylene polymer, or a hydrophobic polymeric substituent such as a poly (lactic acid) group, a poly(lactide-co-glycolide) group or a poly (glycolic acid) group. The X groups may be linear, branched or cyclo groups. Any of the X groups may be directly linked to the d unit (i.e. at the C2 of the monomer unit), or via a functional group such as an amine group, an acyl group, or an amide group, thereby forming linkages that may be represented as X'-ring, X'—NH—, X'—CO-ring, X'CONH-ring, where X' is the hydrophobic group as defined above.

Preferred examples of X groups include those represented by the formulae $CH_3(CH_2)_n$—CO—NH— or $CH_3(CH_2)_n$—NH— or the alkeneoic acid $CH_3$ $(CH_2)_p$—CH=CH—$(CH_2)_q$—CO—NH—, where n is between 4 and 30, and more preferably between 6 and 20, and p and q may be the same or different and are between 4 and 16, and more preferably 4 and 14. A particularly preferred class of X substituents are linked to the chitosan monomer unit via an amide group, for example as represented by the formula $CH_3(CH_2)_n$CO—NH—, where n is between 2 and 28. Examples of amide groups are produced by the coupling of carboxylic acids to the amine group of chitosan. Preferred examples are fatty acid derivatives $CH_3(CH_2)_n$COOH such as those based on capric acid (n=8), lauric acid (n=10), myristic acid (n=12), palmitic acid (n=14), stearic acid (n=16) or arachidic acid (n=18).

In the above formula, $R_1$, $R_2$ and $R_3$ are preferably independently selected from a substituted or unsubstituted alkyl group such as a $C_{1-10}$ alkyl group. $R_1$, $R_2$ and/or $R_3$ may be linear or branched. Preferably, $R_1$, $R_2$ and $R_3$ are independently selected from methyl, ethyl or propyl groups.

In the above formula, $R_8$ and $R_9$ are preferably independently selected from hydrogen and a substituted or unsubstituted alkyl group such as a $C_{1-10}$ alkyl group. $R_8$ and/or $R_9$ may be linear or branched. Preferably, $R_8$ and $R_9$ are independently selected from methyl, ethyl or propyl groups.

In the above formula, $R_4$, $R_5$, $R_6$ and $R_{10}$ present on the C6 or the sugar units are independently selected from hydrogen, a substituted or unsubstituted alkyl group, a substituted or unsubstituted ether group, or a substituted or unsubstituted alkene group. Preferred $R_4$, $R_5$, $R_6$ and $R_{10}$ groups are substituted with one of more hydroxyl groups, or another non-ionic hydrophilic substituent. Examples of $R_4$, $R_5$, $R_6$, and $R_{10}$ groups are represented by the formulae —$(CH_2)_p$—OH, where p is between 1 and 10, and is preferably between 2 and 4, or —$(CH_2)_p$—CH($CH_2$—OH)$_2$ where p is between 1 and 10 or —$(CH2)_p$—C($CH_2$—OH)$_r$ where p is between 1 and 10, and r is 3, or —$(CH_2CH_2OH)_p$, where p is between 1 and 300.

The $R_7$ group may be present or absent in the general formula. When absent, it provides a quaternary ammonium functional group that is directly linked to the monomer unit of the chitosan backbone. When the $R_7$ group is present it may be a unsubstituted or substituted alkyl group (e.g. a $C_{1-10}$ alkyl group) for example as represented by the formula —$(CH_2)_n$—, an amine group as represented by the formula —NH—$(CH_2)_n$—, or an amide group as represented by the formula —NH—CO—$(CH_2)_n$—, where n is 1 to 10 and is preferably 1 to 4. A preferred example of the $R_7N^+R_1R_2R_3$ substituent is provided by coupling betaine (—OOC—$CH_2$—N—$(CH_3)_3$) to the amine substituent of the b unit providing an amide group such as in: —NH—CO—$CH_2$—$N^+R_1R_2R_3$.

As indicated, some of the substituents described herein may be either unsubstituted or substituted with one or more additional substituents as is well known to those skilled in the art. Examples of common substituents include halo; hydroxyl; ether (e.g., $C_{1-7}$ alkoxy); formyl; acyl (e.g. $C_{1-7}$ alkylacyl, $C_{5-20}$ arylacyl); acylhalide; carboxy; ester; acyloxy; amido; acylamido; thioamido; tetrazolyl; amino; nitro; nitroso; azido; cyano; isocyano; cyanato; isocyanato; thiocyano; isothiocyano; sulfhydryl; thioether (e.g., $C_{1-7}$ alkylthio); sulphonic acid; sulfonate; sulphone; sulfonyloxy; sulfinyloxy; sulfamino; sulfonamino; sulfinamino; sulfamyl; sulfonamido; $C_{1-7}$ alkyl (including, e.g., unsubstituted $C_{1-7}$ alkyl, $C_{1-7}$ haloalkyl, hydroxyalkyl, carboxyalkyl, $C_{1-7}$ aminoalkyl, $C_{5-20}$ aryl-$C_{1-7}$ alkyl); $C_{3-20}$ heterocyclyl; and $C_{5-20}$ aryl (including, e.g., $C_{5-20}$ carboaryl, $C_{5-20}$ heteroaryl, alkyl-$C_{5-20}$ aryl and $C_{5-20}$ haloaryl) groups.

The term "ring structure" as used herein, pertains to a closed ring of from 3 to 10 covalently linked atoms, yet more preferably 3 to 8 covalently linked atoms, yet more preferably 5 to 6 covalently linked atoms. A ring may be an alicyclic ring, or aromatic ring. The term "alicyclic ring," as used herein, pertains to a ring which is not an aromatic ring.

The term "carbocyclic ring", as used herein, pertains to a ring wherein all of the ring atoms are carbon atoms.

The term "carboaromatic ring", as used herein, pertains to an aromatic ring wherein all of the ring atoms are carbon atoms.

The term "heterocyclic ring", as used herein, pertains to a ring wherein at least one of the ring atoms is a multivalent ring heteroatom, for example, nitrogen, phosphorus, silicon, oxygen or sulphur, though more commonly nitrogen, oxygen, or sulphur. Preferably, the heterocyclic ring has from 1 to 4 heteroatoms.

The above rings may be part of a "multicyclic group".

Preferably, the amphiphilic carbohydrate compound is quaternary ammonium palmitoyl glycol chitosan (GCPQ).

The amphiphilic carbohydrate compound is capable of self-assembling into particles in aqueous media without the presence of other agents such as tripolyphosphate.

The compositions of the present invention may form particulate aggregates. These may be formed by the aggregation of individual amphiphile molecules and the hydrophilic drug and have a mean particle size of between 10 nm and 20 µm.

Preferably the amphiphilic carbohydrate compound forms nanoparticles which can be loaded with hydrophilic drug. A dispersion of carbohydrate and drug may be formed which is clear or translucent. Generally the amphiphilic compound is mixed with drug and a dispersion is prepared by vortexing and probe sonicating the mixture.

The mean particle size can readily be determined microscopically or by using photon correlation spectroscopy and is conveniently determined in aqueous dispersions prior to filtration. More preferably, the polymeric micellar aggregates have a minimum mean particle size of at least 10 nm, and more preferably at least 30 nm, and a maximum mean particle size which is preferably 10 µm or less.

Typically, the ratio of amphiphilic carbohydrate compound to drug is within the range of 1:10-20:1; a preferred range is 0.5:1-10:1 and a more preferred ratio is 1:1 by weight.

Typically, the ratio of amphiphilic carbohydrate compound to drug to pharmaceutically acceptable carrier may be about 1-100 mg: 50 mg: 1 g.

The pharmaceutical composition of this invention may be in a liquid or solid form suitable for intranasal administration.

A suitable daily dose can be determined based on age, body weight, administration time, etc. While the daily doses may vary depending on the condition and body weight of the patient, and the nature of the drug, a typical intranasal dose is about 0.1-120 mg/person/day, preferably 0.5-60 mg/person/day.

The invention will now be illustrated by the following Examples, which refer to FIGS. 1 and 2, wherein.

EXAMPLES

Example 1

Synthesis of Quaternary Ammonium Palmitoyl Glycol Chitosan (GCPQ) Acid Degradation of Glycol Chitosan Glycol chitosan (2 g) was dissolved in hydrochloric acid (4M, 150 mL) for 20 mins a room temperature under constant stirring. The solution was placed in a preheated water bath at 50° C. At 8 hr the reaction was stopped and the product was removed from the shaking water bath. Molecular weight was controlled by degradation time, i.e. increasing the acid degradation time decreased the molecular weight of the resulting polymer. Previous work has shown that a molecular weight of 13,000 Da was obtained after 8 hr of acid hydrolysis of glycol chitosan with a starting molecular weight of approximately 100,000 Da. The product was purified by exhaustively dialysing (Visking seamless cellulose tubing, molecular weight cut off of 7,000 Da) against deionised water (5 L) with six changes over 24 hr. The dialysate at the end of the dialysis procedure (neutral pH) was subsequently freeze-dried, and the product was recovered as a cream-colored cotton-wool-like material. The degradation yielded 1.06 g (i.e. 53%) of degraded glycol chitosan.

Palmitoylation of Degraded Glycol Chitosan

Degraded glycol chitosan (500 mg) and sodium bicarbonate (376 mg, ~0.045M) were dissolved in a mixture of absolute ethanol (24 mL) and deionised water (76 mL). To this glycol chitosan solution was added dropwise a solution of palmitic acid N-hydroxysuccinimide (PNS, 792 mg) dissolved in absolute ethanol (150 mL), with continuous stirring over a period of 20 mins. The mixture was then stirred for 72 hr and the product isolated by evaporating off most of the ethanol and extracting 3 times the remaining aqueous phase (100 mL) with diethylether (each time twice the volume of the aqueous phase i.e. 200 mL was used). The aqueous mixture of the polymer was exhaustively dialysed (Visking seamless cellulose tubing, molecular weight cut off=7,000 Da) against deionised water (5 L) with 6 changes over a 24-hr period and the resultant product freeze-dried to give a white cotton-like solid.

Quaternisation of Palmitoyl Glycol Chitosan

Palmitoyl glycol chitosan (300 mg) was dispersed in N-methyl-2-pyrrolidone (25 mL) overnight for 12 hr at room temperature. Sodium hydroxide (40 mg, 1 mole as an aqueous solution 0.057M), methyl iodide (1.0 g, 0.44 mL) and sodium iodide (45 mg, as an ethanolic solution, 0.05M) were added and the reaction stirred under a stream of nitrogen at 36° C. for 3 hr.

The quaternary ammonium product was precipitated with diethyl ether (400 mL), filtered and washed twice more with copious amounts of diethyl ether (twice with 300 mL) to give a yellow hygroscopic solid. The quaternised product was dissolved in water (100 mL) to give a yellow solution. The resultant solution was exhaustively dialysed against water (5 L) with six changes over a 24 hr period and the dialysate was passed through a column (1×6 cm) packed with Amberlite IRA-96 Cl$^-$. The column was packed with one volume of the resin (30 mL) and subsequently washed with hydrochloric acid solution (90 mL, 1M) followed by deionised water (10 L) to give a neutral pH. The clear eluate from the column was freeze-dried to give quaternary ammonium palmitoyl glycol chitosan (GCPQ) as a transparent fibrous solid. The synthetic yield of GCPQ is between 150-160 mg (i.e. 50-53%).

Gel Permeation Chromatography and Multi-Angle Laser Light Scattering (GPC-MALLS)

The molecular weight of GCPQ was determined by GPC-MALLS equipped with DAWN® EOS™ MALLS ($\lambda$=690 nm), Optilab DSP Interferometric Refractometer ($\lambda$=690 nm) and both quasi-elastic light scattering and light scattering detectors (Wyatt Technology Corporation, USA) using a mobile phase of acetate buffer (0.3 M $CH_3COONa$ (anhydrous)/0.2 M $CH_3COOH$, pH=4.5)/HPLC grade Methanol (35:65) at a flow rate 1 ml min$^{-1}$. Filtered samples (0.2 μm) were injected using a Waters 717 Autosampler into a POLYSEP™-GFC-P guard column (35×7.8 mm, Phenomenx, UK) attached to a POLYSEP™-GFC-P 4000 column (300×7.8 mm, Phenomenx, UK) at a loading concentration of 5 mg mL$^{-1}$. The data was processed using ASTRA for windows version 4.90.08 software (Wyatt Technology Corporation, USA). The specific refractive index increment (dn/dc) of GCPQ was measured in solvent (as above) at room temperature with an Optilab DSP Interferometric Refractometer ($\lambda$=690 nm). Filtered samples (0.2 μm) ranging from 0.1-0.6 mg mL$^{-1}$ were manually injected using an Injection System (Wyatt Technology Corporation, USA) at a pump flow rate of 0.3 mL min$^{-1}$. The data was processed using ASTRA for windows version 4.90.08 software (Wyatt Technology Corporation, USA).

$^1$H NMR $^1$H NMR experiments were performed on a Bruker AMX 400 MHz spectrometer (Bruker Instruments, Coventry, U.K.) of acid degraded chitosan in $D_2O$ (10 mg mL$^{-1}$) and GCPQ solutions in $CH_3OD$ (10 mg mL$^{-1}$). Analyses were performed at a temperature of 45-50° C. The level of palmitoylation was calculated by comparing the ratio of palmitoyl methyl protons ($\delta$=0.89 ppm) to sugar protons ($\delta$=3.5-4.5 ppm) and the level of quaternisation calculated by comparing the ratio of quaternary ammonium ($\delta$=3.45 ppm) to sugar protons.

Preparation of Self Assembled Polymer Nanoparticles

Self-assembled polymer amphiphiles were prepared by vortexing (WhirliMixer, Fisherbrand) GCPQ (45 mg) in water for injection BP (B. Braun Melsungen AG, Germany)

(1.5 mL) and then by probe sonicating the dispersion (Qsonica) with the instrument set at 30% of its maximum output for 10 minutes on ice. Particle size was measured by Photon correlation spectroscopy (Malvern Zetasizer 3000HS, Malvern Instruments, UK) at 25° C. at a wavelength of 633 nm and the data analysed using the Contin method of data analysis. Polymer dispersions were left for 15 mins at room temperature (25° C.) before particle size was measured. The clear dispersions were then syringe-filtered (0.45 µm, 33 mm Millex GP syringe driven filter unit, PES membrane for sterilisation of aqueous solutions) and the filtered solution was then measured again as above. Measurements were performed in triplicate.

The morphological examination of the nanoparticles was studied by transmission electron microscopy (TEM). A drop of unfiltered solution was placed on Formvar/Carbon Coated Grid (F1961100 3.05 mm, Mesh 300, Tab Labs Ltd, UK). Excess sample was filtered off with No. 1 Whatman Filter paper and negatively stained with 1% aqueous Uranyl Acetate. Imaging was carried out using an FEI CM120 BioTwin Transmission Electron Microscope (FEI, USA). Digital Images were captured using an AMT digital camera. Polymer nanoparticles (unfiltered) presented a spherical morphology.

Preparation of Self Assembled Polymer NanoParticles (with Drug) for Nasal Administration GCPQ dispersions (30 mg mL$^{-1}$) with LENK (30 mg mL$^{-1}$) were prepared by vortexing (WhirliMixer, Fisher, UK) for 5 minutes in water for injection BP (B. Braun Melsungen AG, Germany) the suspension was then pH adjusted to pH=5.8 with 1M NaOH prior to probe sonicating (Qsonica) with the instrument set at 30% of its maximum output for 10 minutes on ice (pH=5.8). Formulations were filtered (0.8 µm, 13 mm, Acrodisc Syringe Filter, Super Low Protein Binding Non-Pyrogenic Membrane, PALL Life Science). Formulations were left overnight in the fridge. Particle size was measured by Photon correlation spectroscopy (Malvern Zetasizer 3000HS, Malvern Instruments, UK) at 25° C. at a wavelength of 633 nm and the data analysed using the Contin method of data analysis. Polymer dispersions with LENK were left for 15 mins at room temperature (25° C.) before particle size was measured. The morphological examination of the nanoparticles was studied with TEM. A drop of unfiltered solution was placed on Formvar/Carbon Coated Grid (F1961100 3.05 mm, Mesh 300, Tab Labs Ltd, UK). Excess sample was filtered off with No. 1 Whatman Filter paper and negatively stained with 1% aqueous Uranyl Acetate. Imaging was carried out under a FEI CM120 BioTwin Transmission Electron Microscope (FEI, USA). Digital Images were captured using an AMT digital camera. Polymer nanoparticles (unfiltered) presented a spherical morphology.

Analysis of Peptide Drug Loaded Polymers

The quantitative determination of LENK was performed on an Agilent high performance liquid chromatography (HPLC) system consisting of a binary pump (1220 Infinity LC Gradient System VL) equipped with a variable wavelength UV detector and with an Onyx monolithic C18 column (5 µm, 4.6 mm×10 mm) with a C18 guard column (Phenomenex, UK). The mobile phase consisted of 82% water: 18% acetonitrile: 0.02% trifluoroacetic acid. Sample elution was monitored at a UV absorption wavelength of 214 nm, at a flow rate of 1.0 mL min$^{-1}$ at 30° C. with an injection volume of 10 The retention time was 6.6 minutes for LENK and the lowest detection limits were 1 µg mL$^{-1}$.

Results for Peptide Drug Loaded Polymer Dispersions for Intranasal Administration Drug-Polymer dispersions presented as clear or translucent formulations and consisted of two populations of particles which had sizes of 20 nm and 500 nm. The drug content was analysed at 80% of the initial amount.

In Vivo Studies Intranasal Administration Pharmacodynamics-Animals

Sprague Dawley rats (200-250 g) were housed four per cage in an air conditioned unit maintained at 20-22° C. and 50-60% humidity and were allowed free access to standard rodent chow and water. Lighting was controlled on a twelve-hour cycle, lights on at 07.00 h. Animals were habituated for 7 days prior to experimentation and acclimatised to the procedure room for 1 hr prior to testing. All protocols were conducted under a UK Home office licence and approved by a local ethics committee.

Formulations

Rats were intranasally administered water for injection (0.05 ml), intranasal LENK hydrochloride salt in water 30 mg mL$^{-1}$, (7.5 mg kg$^{-1}$, pH=5.8, 50 µL), GCPQ-LENK in water composed of LENK hydrochloride salt 30 mg mL$^{-1}$, (7.5 mg kg$^{-1}$, pH=5.8, 50 µL) and GCPQ (30 mg mL$^{-1}$). The administered intranasal volume of the formulations was set to a maximum of 60 µL per rat. The administered volume was adjusted based on the high performance liquid chromatography (HPLC) quantification of LENK and the body weight of each animal. The maximum volume was dosed for placebo (water pH=5.8) receiving rats. Animals were briefly anesthetised with isoflurane and intranasally administered formulations using an insulin syringe attached to PE10 tubing (15 mm), the tubing was inserted into one of nares.

Complete Freund's Adjuvant (CFA) Induced Chronic Inflammatory Pain

Rats received an intraplantar injection of 100 µL of CFA (*Mycobacterium tuberculosis* heat killed suspended in 85% paraffin oil and 15% mannide monooleate 1 mg/ml, Sigma) using a glass Hamilton syringe with a 25 G needle. CFA caused hind paw oedema and mechanical hypersensitivity was evaluated 24 hr after CFA injection.

Measurement of Mechanical Hypersensitivity

Mechanical hypersensitivity was evaluated. Rats were individually placed on an elevated plastic mesh (0.5 cm$^2$ perforations) in a clear plastic cage. Two habituations to the evaluation chambers for at least 5 min duration each were performed on two different days. A baseline measurement was taken on test day pre-CFA. Mechanical hypersensitivity was assessed by the sensitivity to the application of von Frey hairs (Ugo Basile, Switzerland). The von Frey filaments (1.4, 2, 4, 6, 8, 10, 15, 26 g) were presented perpendicularly to the plantar surface of the injected paw in ascending order, and held in this position for 5 s with enough force to cause a slight bend in the filament. Positive responses included an abrupt withdrawal of the hind paw or a response was noted if the paw was sharply withdrawn or there was flinching upon application of the hair. Once a positive withdrawal response was established, the paw was retested, starting with the next descending von Frey hair until no response occurred. The lowest amount of force required to elicit a response was recorded as the paw withdrawal (g). Mechanical allodynia was defined as a significant decrease in withdrawal thresholds to von Frey hairs application. The 26 g hair was selected as the upper limit cut-off for testing.

To test formulation effects on mechanical allodynia, rats were evaluated for thresholds 24 hr after CFA injection; they were then randomised according to their threshold values and dosed with formulations. Rats were evaluated by an observer blinded to the treatments.

Central and Peripheral Contributions to Analgesia

To assess the contribution of central and peripheral mechanisms of formulation analgesia, non-selective opioid antagonists were administered subcutaneously. naloxone hydrochloride (15 mg mL$^{-1}$, 7.3 mg kg$^{-1}$ 90 μL, MP Biomedicals, UK) and naloxone methiodide quaternary ammonium salt of naloxone which is peripherally restricted (20 mg mL$^{-1}$, 10 mg kg$^{-1}$, 90 μL, Sigma). These antagonists were concomitantly administered with nasal formulations.

Statistical Analysis

Results are presented as mean±S.E.M. and the data were analyzed by two-way analysis of variance (ANOVA) followed by Bonferroni post hoc test. All statistical analyses were performed using GraphPad Prism 5.0 (GraphPad Software, San Diego, Calif.). P values of less than 0.05 were considered significant.

Pharmacodynamics Results

Figure 1:
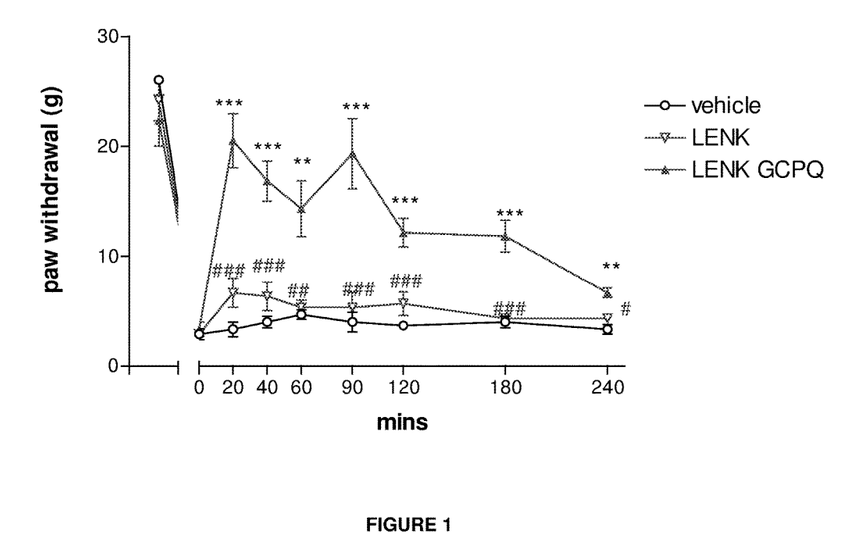
FIG. 1 shows the effect of intranasal LENK in the absence and presence of GCPQ in a Complete Freund's Adjuvant (CFA) rat inflammatory pain model.

FIG. 1 shows the effect of intranasal LENK in the absence and presence of GCPQ in a rat CFA inflammatory pain model (mean±SEM n=6; two way ANOVA with repeated measure followed by Bonfferoni post hoc test). In FIG. 1, * represents a statistically significant difference between the vehicle and treatment groups, and # represents a statistically significant difference between LENK alone and LENK-GCPQ.

100 μL CFA was injected into the plantar surface of the left back paw. Inflammation was allowed to develop for 24 hr. Animals were randomised on the post-CFA baseline prior to receiving an intranasal administration of vehicle (water, 50 μL/rat), LENK 7.5 mg kg$^{-1}$ (pH=5.8, 50 μL), LENK-GCPQ (7.5 mg kg$^{-1}$ LENK and 7.5 mg kg$^{-1}$ GCPQ, pH=5.8, 50 μL). GCPQ19082013LG (mole % palmitoylation=13%, mole % quaternary ammonium groups=9.1%, molecular weight=22 KDa, Mw/Mn=1.031). Paw withdrawal to von Frey hairs (1.4, 2, 4, 6, 8, 10, 15, 26 g) was assessed 20 min, 40 min, 1, 2, 3 and 4 hr using the up-down method of assessment.

Pre-CFA baseline paw withdrawal force was 24.4±4 g. Post-CFA (24 hr) baseline was 3.3±1.3 g. No statistical difference was observed between LENK solution (30 mg mL$^{-1}$) and the vehicle control at any of the time points measured (20, 40 min, 1, 1.5, 2, 3 and 4 hr). The LENK-GCPQ (30 mg mL$^{-1}$ LENK) formulation significantly reversed the nociception for up to 4 hr, in comparison to the vehicle control and the LENK solution.

To assess the contribution of central and peripheral mechanisms of action, the non-specific opioid antagonists naloxone and its peripherally restricted quaternary ammonium salt, naloxone methioide, were used.

Figure 2:
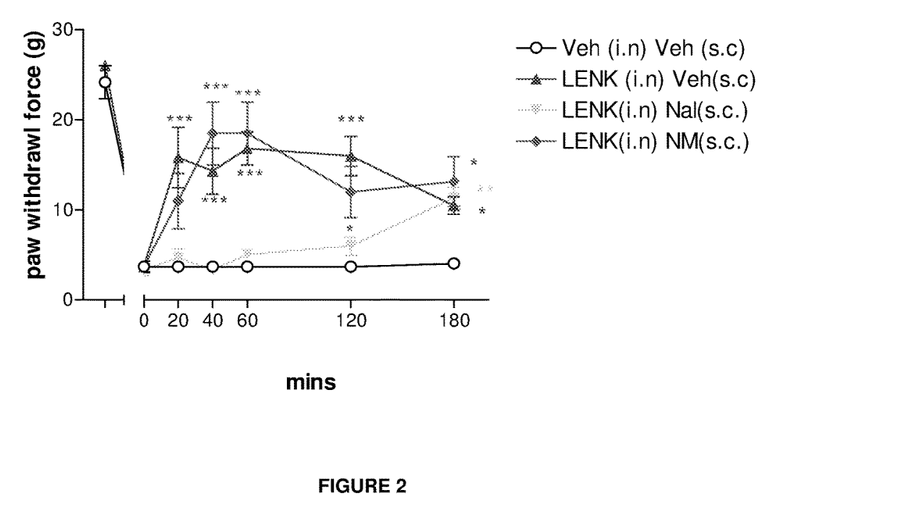
FIG. 2 shows assessment of the contribution of central and peripheral mechanisms to the activity of an intranasal LENK-GCPQ formulation in a rat CFA inflammatory pain model.

FIG. 2 illustrates the assessment of the contribution of central and peripheral mechanisms of action of intranasal LENK-GCPQ formulations in CFA inflammatory pain rats (mean±SEM n=6, two way ANOVA with repeated measure followed by Bonfferoni post hoc test). In this figure * represents a statistically significant difference between the vehicle and treatment groups.

100 μL CFA was injected into the plantar surface of the left back paw. Inflammation was allowed to develop for 24 hr. Animals were randomised on the post-CFA baseline prior to receiving an intranasal administration of vehicle (water, 50 μL/rat) or LENK-GCPQ (7.5 mg kg$^{-1}$ LENK and 7.5 mg kg$^{-1}$ GCPQ, pH=5.8, 50 μL). GCPQ25092013LG (mole % palmitoylation=15.5%, mole % quaternary ammonium groups=8.7%, molecular weight=20 KDa, Mw/Mn=1.061). Concomitantly subcutaneous injections were also administered; vehicle (water for injection, 90 μL), opioid antagonist Naloxone (NaI 7.3 mg kg$^{-1}$ subcutaneously, 90 μL) or the peripherally restricted opioid antagonist Naloxone Methiodide (NM, 10 mg kg$^{-1}$, subcutaneously 90 μL). Paw withdrawal to von Frey hairs (1.4, 2, 4, 6, 8, 10, 15, 26 g) was assessed 20 min, 40 min, 1, 2, and 3 hr using the up-down method of assessment.

As previously shown LENK-GCPQ formulation was antinociceptive at all time points measured (20, 40 min, 1, 2 and 3 hr) in the absence of antagonist. In the presence of Naloxone LENK-GCPQ antinociception was completely abolished up to 2 hr. At the 3 hr time point antinociception returned presumably due to the short half-life of Naloxone. In contrast, in the presence of the peripherally restricted antagonist, Naloxone methiodide, LENK-GCPQ antinociception was completely unaffected therefore indicating that there is no peripheral mechanism involved in the antinociception of LENK GCPQ.

Example 2—Comparison of Invention with Prior Art

Methods

Trimethylchitosan Synthesis 2-Step Reaction (Prior Art)

Two step synthesis was carried out using essentially the same method as reported by Sieval, A. B., et al., *Preparation and NMR characterization of highly substituted N-trimethyl chitosan chloride*. Carbohydrate polymers, 1998. 36(2-3): p. 157-165. Briefly 2 g chitosan (Sigma, UK) was suspended in 80 ml of 1-methyl-2-pyrrolidinone in 3 neck flask, in a stabilised oil bath at 60° C. under reflux. Sodium iodide (4.8 g) was dissolved in 11 ml of NaOH (15%, 3.84M) and added to the chitosan. The system was purged of air with nitrogen prior to the addition of methyl iodide (11.5 ml) and reacted for 1 hr. The product was precipitated with ethanol and thereafter isolated by centrifugation (2000 rpm at 6° C. for 3 min). The product was placed in a vacuum filter and washed twice with ether (300 ml total) to remove all the ethanol until it was quite dry. The product was then resuspended in NMP (80 ml) stirring for 30 mins at 60° C. uncapped to remove the majority of the ether. Subsequently, 4.8 g sodium iodide and 11 ml of 15% NaOH solution, and 7 ml of methyl iodide was added and the reaction and stirred under reflux for 30 mins. A further addition of methyl iodide (5 ml) and 0.6 g NaOH pellets were added to the reaction which continued for a further 90 mins. The reaction mixture was precipitated with ethanol as before and centrifuged to isolate, the ethanol was removed and the product was washed with ether (100 ml). The product was left overnight to dry and resuspended in NaCl (40 ml, 10%). This was then dialysed and freeze dried. $^1$H NMR spectra were measured in D$_2$O at 80° C. using AV400 MHz spectrometer.

TMC Synthesis 1—Step Reaction

One step synthesis was carried out using essentially the same method as reported by Sieval et al mentioned above. Briefly 2 g chitosan, 4.8 g sodium iodide were suspended in 80 ml of NMP in 3 neck flask, in a stabilised oil bath at 60° C. under reflux (3 hrs). Once dissolved 11 ml of NaOH (15%, 3.84M, 2.8 g/18.6 ml) followed by 11.5 ml methyl iodide were added. The reaction was stirred for 1 hr. The product was precipitated with ethanol and thereafter isolated by centrifugation (2000 rpm at 6° C. for 3 min). The material was dissolved in 40 ml water to which 250 ml 1 M HCL in ethanol was added and stirred overnight. The product was isolated by centrifugation (2000 rpm at 6° C. for 3 min) and the pellet washed twice with ethanol and isolated by centrifugation. The product was placed in a vacuum filter and washed twice with ether (300 ml total). The semi-dry product was resuspended in water and dialysed for 24 hrs with 6 changes. Product was freeze dried.

¹H NMR

¹H NMR experiments were performed on a Bruker AV 400 MHz spectrometer (Bruker Instruments, Coventry, U.K.) of TMC in $D_2O$ (10 mg/ml). Analyses were performed at a temperature of 80° C. with suppression of the water peak. The degree of methylation was calculated as a percentage, $$\% DQ = \frac{[(CH_3)_3]}{[H] \times 1/9} \times 100$$

$[(CH_3)_3]$ is the integral of the chemical shift of the trimethyl amino group at 3.3 ppm, and [H] is the integral of the ¹H peaks between 4.7 and 5.7 ppm (Polnok, A., et al., Influence of methylation process on the degree of quaternization of N-trimethyl chitosan chloride. European journal of pharmaceutics and biopharmaceuticals: official journal of Arbeitsgemeinschaft fur Pharmazeutische Verfahrenstechnik e.V, 2004. 57(1): p. 77-83.)

TMC Particles (40% Methylation)

TMC laded particles were prepared as Kumar, M., et al., *Evaluation of neuropeptide loaded trimethyl chitosan nanoparticles for nose to brain delivery.* International journal of biological macromolecules, 2013. 61C: p. 189-195. 24 mg TMC (40%) in 12 ml water with 138 mg LENK base. 7.3 ml TPP (0.6 mg/ml) dropped into the stirred TMC through 16 G needle. The formulation was stirred overnight. Nanoparticles were pelleted by centrifugation (12000×g 30 mins at 8° C.). The supernatant was analysed for LENK content and the pellet resuspended in 0.3 ml injection water 9.6 mg/0.3 ml=32 mg/ml, pH6. Particle size was measured by Photon Correlation Spectroscopy (Malvern Zetasizer 3000HS, Malvern Instruments, UK) at 25° C. at a wavelength of 633 nm and the data analysed using the Contin method of data analysis. The morphological examination of the nanoparticles was studied with TEM. A drop of unfiltered solution was placed on Formvar/Carbon Coated Grid (F1961100 3.05 mm, Mesh 300, Tab Labs Ltd, UK). Excess sample was filtered off with No. 1 Whatman Filter paper and negatively stained with 1% aqueous Uranyl Acetate. Imaging was carried out under a FE1 (Ex. Philips) CM120 BioTwin Transmission Electron Microscope (TEM). Digital Images were captured using an AMT (digital) camera. Polymer nanoparticles (unfiltered) presented a spherical morphology.

TMC Particles (15% Methylation)

TMC laded particles were prepared as Kumar et al *Evaluation of neuropeptide loaded trimethyl chitosan nanoparticles for nose to brain delivery.* International journal of biological macromolecules, 2013. 61C: p. 189-195. 29 mg TMC (15%) in 14.5 ml water with 125 mg LENK base. 8.78 ml TPP (0.6 mg/ml) was dropped into the stirring TMC through 16 G needle. Nanoparticles were pelleted by centrifugation (12000×g 30 mins 8° C.). The formulation was stirred overnight. The supernatant was analysed for LENK content (HPLC) and the pellet resuspended in 0.3 ml injection water 6.1 mg/0.3 ml=20 mg/ml, adjusted from pH 4 to pH 5 with NaOH. Nanoparticles size and morphology were analysed as above.

Preparation of Self Assembled Polymer NanoParticles

Polymer dispersions (30 mg/mL) with LENK (30 mg/mL) were prepared according to Example 1.

Pharmacodynamics

Nasal dosing and mechanical hypersensitivity was assessed as before.

Results for Peptide Drug Loaded Polymer Dispersions for Intranasal Administration Drug-Polymer dispersions presented as a slight opalescent suspension with a 24-40% loading efficiency. z-average mean of 855.2±19.85 nm and 601.6±89.2 nm for 40% and 15% methylated chitosan respectively with a polydispersity index=0.292 and 0.659 respectively.

Measurement of Paw Withdrawal Force

100 μCFA was injected into the plantar surface of the left back paw. Inflammation was allowed to develop for 24 hr. Animals were randomised on the post-CFA baseline prior to receiving intranasal administration of vehicle (water pH 50 μl/rat), LENK:GCPQ 7.5 mg/kg LENK: 7.5 mg/kg GCPQ (pH 5.8, 50 μl), trimethylchitosan (TMC, 15% methylation) equivalent dose 5 mg/kg, TMC (40% methylation, equivalent LENK dose of 7.5 mg/kg. GCPQ (Batch #09062014AI, degree of palmitoylation=21.54 mole %, degree of quaternisation=12.08 mole %, Mw 16.2 KDa, Mn 15.9 KDa, Mw/Mn 1.018). The paw withdrawal to Von Frey hairs fibres (1.4, 2, 4, 6, 8, 10, 15, 26 g) was assessed at 30 min, 1, 1.5, 2, 3 and 4 hr using the up down method of assessment.

Pharmacodynamics Results

Pre-CFA baseline paw withdrawal force was 24.6±3.7 g. Post-CFA (24 hr) baseline was 4.8±1.3 g. No statistical difference was observed between TMC 15% and the vehicle control at any of the time points measured (30 min, 1, 1.5, 2, 3 and 4 hr). TMC 40% was significantly different at the 30 min time point only. The LENK-GCPQ (30 mg/ml LENK) formulation significantly reversed the nociception for up to 3 hr, in comparison to the vehicle control.

Intranasal LENK GCPQ was a superior anti-nociceptive agent when compared to intranasal TMC LENK.

The following table shows the effect of intranasal LENK GCPQ vs TMC LENK in CFA inflammatory pain in rats. The values are paw withdrawal force, given in g.

|   | VEHICLE | LENK GCPQ |   | TMC 15% |   | TMC 40% |   |
|---|---|---|---|---|---|---|---|
| −24 h | 24.2 ± 1.8 | 24.2 ± 1.8 |   | 24.2 ± 1.8 |   | 26.0 ± 0.0 |   |
| 0 | 4.7 ± 0.8 | 5.0 ± 0.4 |   | 5.0 ± 0.5 |   | 4.8 ± 0.4 |   |
| 0.5 | 5.0 ± 0.4 | 18.7 ± 2.3 | ** | 7.3 ± 0.8 |   | 10.8 ± 1.6 | * |
| 1 | 4.3 ± 0.3 | 14.3 ± 2.5 | * | 5.3 ± 0.4 | # | 7.8 ± 1.7 |   |
| 1.5 | 4.7 ± 0.4 | 14.0 ± 2.7 |   | 5.3 ± 0.4 |   | 4.4 ± 0.4 |   |
| 2 | 4.7 ± 0.4 | 9.7 ± 0.3 | *** | 5.0 ± 0.7 | ## | 4.0 ± 0.0 | ## |
| 3 | 4.0 ± 0.0 | 8.0 ± 0.9 | * | 4.7 ± 0.4 |   | 4.0 ± 0.0 | # |
| 4 | 4.7 ± 0.4 | 7.0 ± 0.7 |   | 5.3 ± 0.4 |   | 4.8 ± 0.4 |   |

Key
Mean ± SEM n = 6. Two way ANOVA with repeated measure followed by Games Howell post hoc test
* = statistically significant difference between the vehicle vs treatment,
# = statistically significant difference between the treatment vs LENK GCPQ

The invention claimed is:

1. A method for treating pain, comprising intranasally administering to a human or animal in need thereof a composition comprising a therapeutically effective amount of a hydrophilic neuroactive peptide and an amphiphilic quaternary ammonium palmitoyl glycol chitosan (GCPQ);
   wherein the amphiphilic GCPQ is capable of self-assembly in aqueous media into particles having a mean particle size between 20-500 nm;
   wherein intranasally administering the composition delivers the hydrophilic neuroactive peptide to the brain of the human or animal.

2. The method according to claim 1, wherein the neuroactive peptide is leucine-enkephalin.

3. The method according to claim 1, wherein the ratio of the amphiphilic GCPQ to the hydrophilic neuroactive peptide in the composition is in the range 0.5:1-10:1 by weight.

4. The method according to claim 1, wherein the drug is hydrophilic neuroactive peptide is an endogenous opioid neuropeptide.

5. The method according to claim 4, wherein the endogenous opioid neuropeptide is a neuropentapeptide.

6. The method according to claim 1, wherein the hydrophilic neuroactive peptide is selected from enkephalin, neuropeptide S, dalargin, orexin, vasopressin, leptin, cholecystokinin, dynorphin, detorphin I, neurotensin, and oxytocin.

7. The method according to claim 1, wherein the treatment is of pain is an inflammatory pain.

8. The method according to claim 1, wherein the composition is in the form of a liquid dispersion.

* * * * *